US007939481B2

(12) United States Patent
Nazzaro

(10) Patent No.: US 7,939,481 B2
(45) Date of Patent: May 10, 2011

(54) COLOR CHANGING BAR SOAP

(76) Inventor: John Nazzaro, Clarksburg, NJ (US)

( * ) Notice: Subject to any disclaimer, the term of this patent is extended or adjusted under 35 U.S.C. 154(b) by 259 days.

(21) Appl. No.: 12/262,379

(22) Filed: Oct. 31, 2008

(65) Prior Publication Data

US 2009/0118156 A1 May 7, 2009

Related U.S. Application Data

(60) Provisional application No. 61/001,493, filed on Oct. 31, 2007.

(51) Int. Cl.
*A61K 7/50* (2006.01)

(52) U.S. Cl. ......... 510/141; 510/143; 510/152; 510/153

(58) Field of Classification Search ........................ None
See application file for complete search history.

(56) References Cited

U.S. PATENT DOCUMENTS

| | | | | |
|---|---|---|---|---|
| 2,677,913 | A | 5/1954 | Swartz | |
| 5,597,556 | A * | 1/1997 | Moghe et al. | 424/65 |
| RE38,946 | E | 1/2006 | Bitton | |
| 2006/0287215 | A1 * | 12/2006 | McDonald et al. | 510/441 |

* cited by examiner

*Primary Examiner* — Necholus Ogden, Jr.
(74) *Attorney, Agent, or Firm* — Porzio, Bromberg & Newman, P.C.

(57) ABSTRACT

A color changing bar soap includes a small toy or figurine located inside a color changing layer such as a bicarbonate shell. The bicarbonate shell is housed within a body of soap. The bicarbonate surrounds and encapsulates the small toy. The soap fully surrounds and encapsulates the bicarbonate layer. The body of soap can be shaped like an egg or other various shapes to be determined, depending on the type of toy to be used with the soaps. In one embodiment, the egg-shaped soap is packaged onto a "nest-like" bail of hay or straw. This is placed inside a wooden or plastic crate for storage and use in a display.

17 Claims, 3 Drawing Sheets

COLOR CHANGING BAR SOAP

CROSS REFERENCE TO RELATED APPLICATION

This application claims the benefit of U.S. Provisional Patent Application No. 61/001,493, filed Oct. 31, 2007, the entirety of which is hereby incorporated by reference into this application.

BACKGROUND OF THE INVENTION

1. Field of the Invention

The present invention generally relates to soaps, combined with water coloring tints and children's toys, preferably plastic toy dinosaurs.

2. Description of the Related Art

Children are known for not wanting to bathe or at times wanting to play with toys while bathing. Many toys are developed for play while taking a bath. Bath toys encourage children to simulate bath time as a good thing and playing with toys during bath time reinforces this.

U.S. Pat. No. 2,677,913 describes a cake of non-floating soap with a figured doll core of sufficiently buoyancy to make the combination float in water. The doll core having the torso embedded in the soap with protruding head and feet to support the soap in an upright position.

RE 38,946 describes a child's toy and soap assembly comprising a small toy or figurine located within a body of transparent soap. A soap container conforming to the shape of the toy receives the body of soap.

It is desirable to provide a shaped color changing bar soap encasing a toy, such as a dinosaur, which during use can release the dinosaur and color the bathwater for increasing the child's interest in bathing and providing an educational experience.

SUMMARY OF THE INVENTION

The purpose of this invention is to get children to have a fin bathing experience and to learn about dinosaurs. In addition to having a fun bathing experience, the child can use the soap until the outer layer exposes an inner color tint layer which then melts into the bath tub coloring the water. In one embodiment, the soap has a hollow egg-shape which can be cracked or peeled open for releasing a toy dinosaur. The change of color creates a sense of excitement for the user.

In one embodiment, a balsa wood container and straw assembly for housing the soap bar acts as a play setting where the child can interact with the dinosaur. Each crate can house an official document which can provide information such as the name of the dinosaur, description feeding habits and other information about it for educational purposes. The child will be able to give the dinosaur a nickname and fill in the blanks to officially give it its name.

The invention will be more fully described by reference to the following drawings.

DETAILED DESCRIPTION

Figure 1:
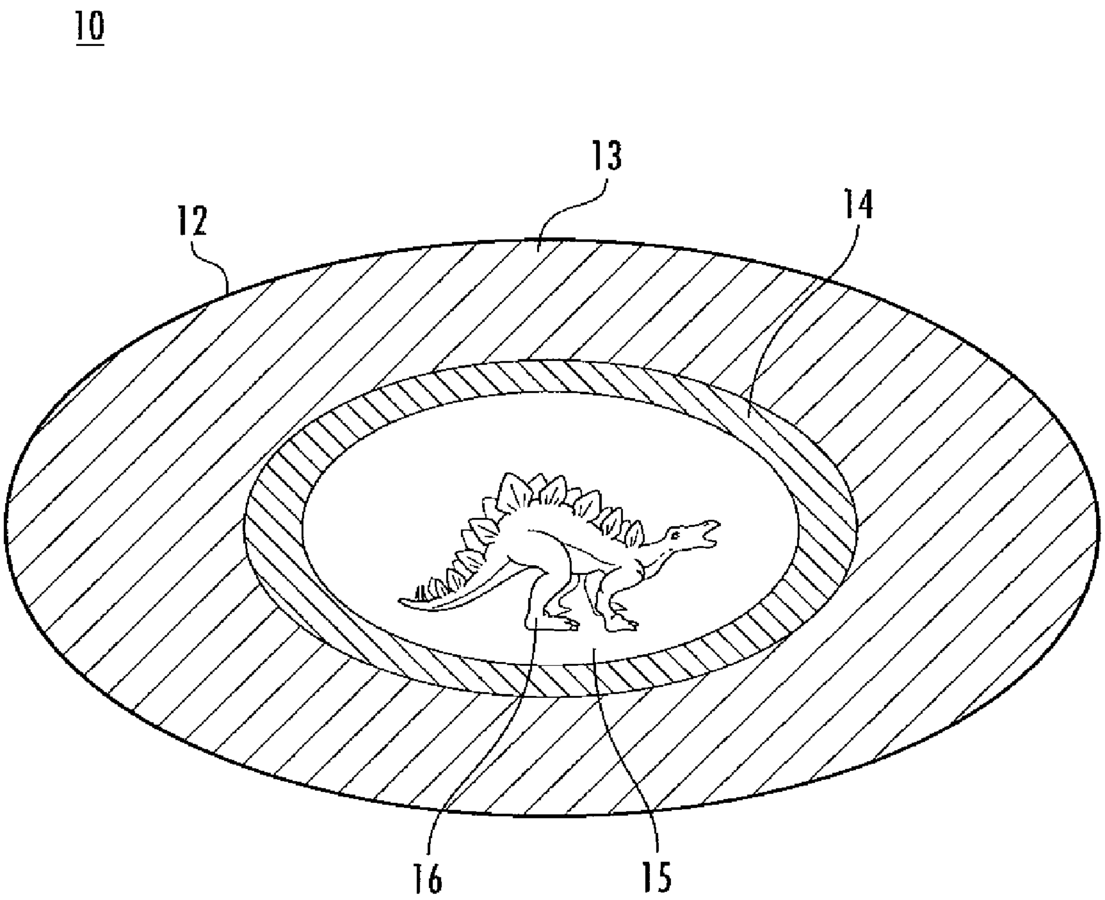
FIG. 1 is a schematic diagram of a color changing bar soap in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a schematic diagram of color changing bar soap 10 in accordance with the teachings of the present invention. Body 12 is formed in a predetermined three-dimensional configuration having a predetermined minimum and maximum width and thickness. For example, body 12 can be formed in the shape of an egg. Body 12 is formed of outer layer 13. Outer layer 13 is formed of a conventional soap. Outer layer 13 is opaque and can be white or colored. Inner layer 14 is positioned adjacent outer layer 13 and toy capsule 15. Toy capsule 15 can include toy 16. Alternatively, inner layer 14 can be formed around toy 16 without toy capsule 15. Preferably, toy capsule 15 and toy 16 are formed of a waterproof material. Example toys 16 can include animals, dinosaurs, vehicles, cars and other collectible or educational toys. The size of the toy, such as the dinosaur, will be large enough to meet the strictest guidelines so as not to be a choking hazard.

Inner layer 14 is formed of a color changing material. For example, the color changing material can be sodium bicarbonate having various color tinting. The color changing material can change the color of the soap, such as the remaining outer layer 13 and/or the water, such as in a tub or sink, when exposed. An example composition of the color changing material is sodium carbonate, sodium bicarbonate, citric acid, lactose, polyethylene glycol, and mineral oil. The tint used for the color changing material can be related to toy 16. For example, a red tint could be used for a meat eater dinosaur, a green tint could be used for a plant eater and a blue tint could be used for a flying dinosaur. Example color tints which can be used in the color changing material include FD&C Blue 1, FD&C Yellow 5, and D&C Red 33.

In one embodiment, toy capsule 16 is about three inches in length. Body 12 is about six inches in length and about four inches in width. Outer layer 13 can have a thickness of about 2 mm. Inner layer 14 can have a thickness of about 2 mm.

Figure 2:
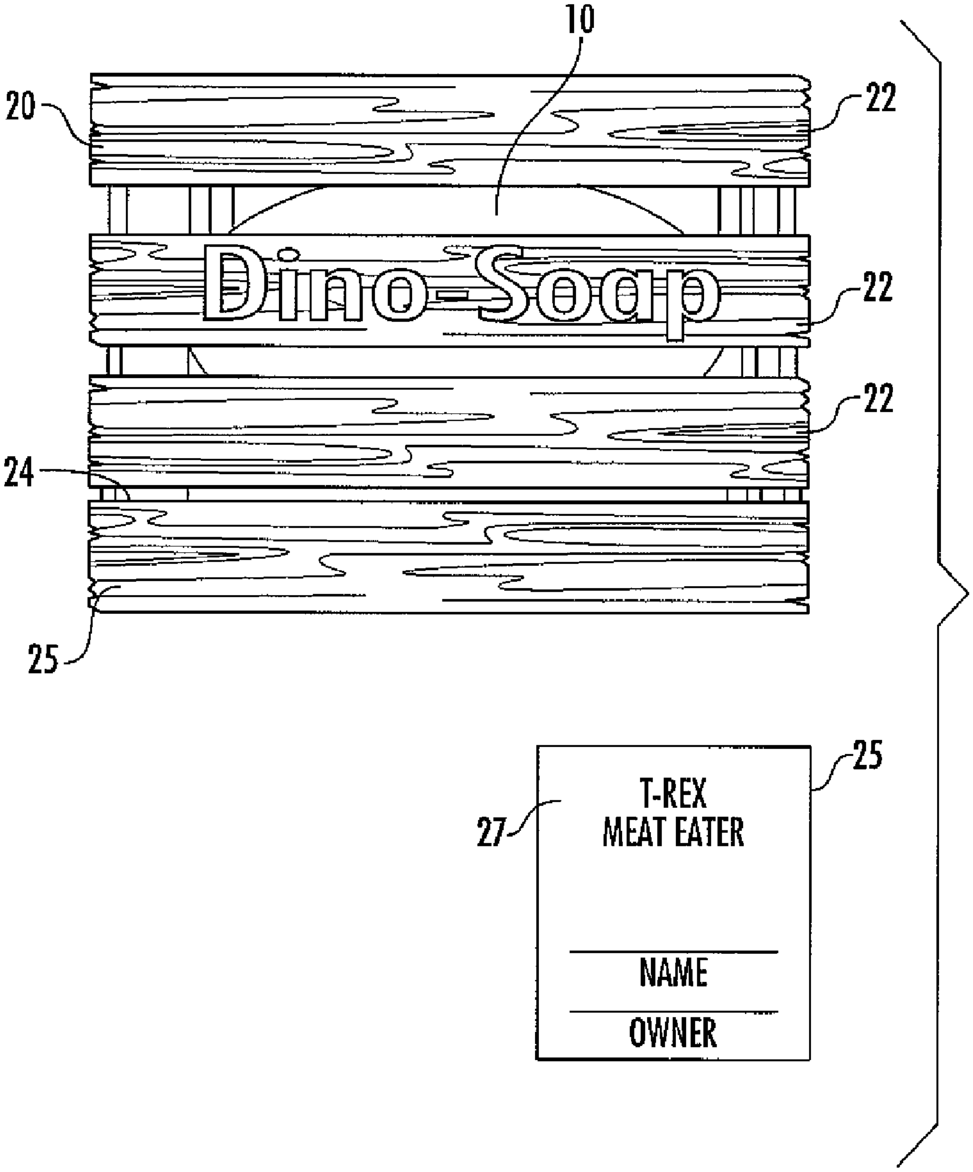
FIG. 2 is a schematic diagram of a housing for the color changing bar soap.

FIG. 2 is a schematic diagram of housing 20 for housing color changing bar soap 10. Housing 20 can be in the form of a crate or box formed of strips 22. For example, strips 22 can be formed of balsa wood. Material 24 can be placed on bottom 25 of housing 20 for cushioning color changing bar soap 10. For example, material 24 can be hay or straw to cushion or support an egg shaped color changing bar soap.

Document 26 can be located within housing. Document 26 can include indicia 27 related to toy 16. Indicia 27 can be informational or educational. For example, indicia 27 can include informational or educational information. For example, if toy 16 is an animal, document 26 can include indicia 27, such as a name, feeding habits and physical traits of the animal.

Figure 3:
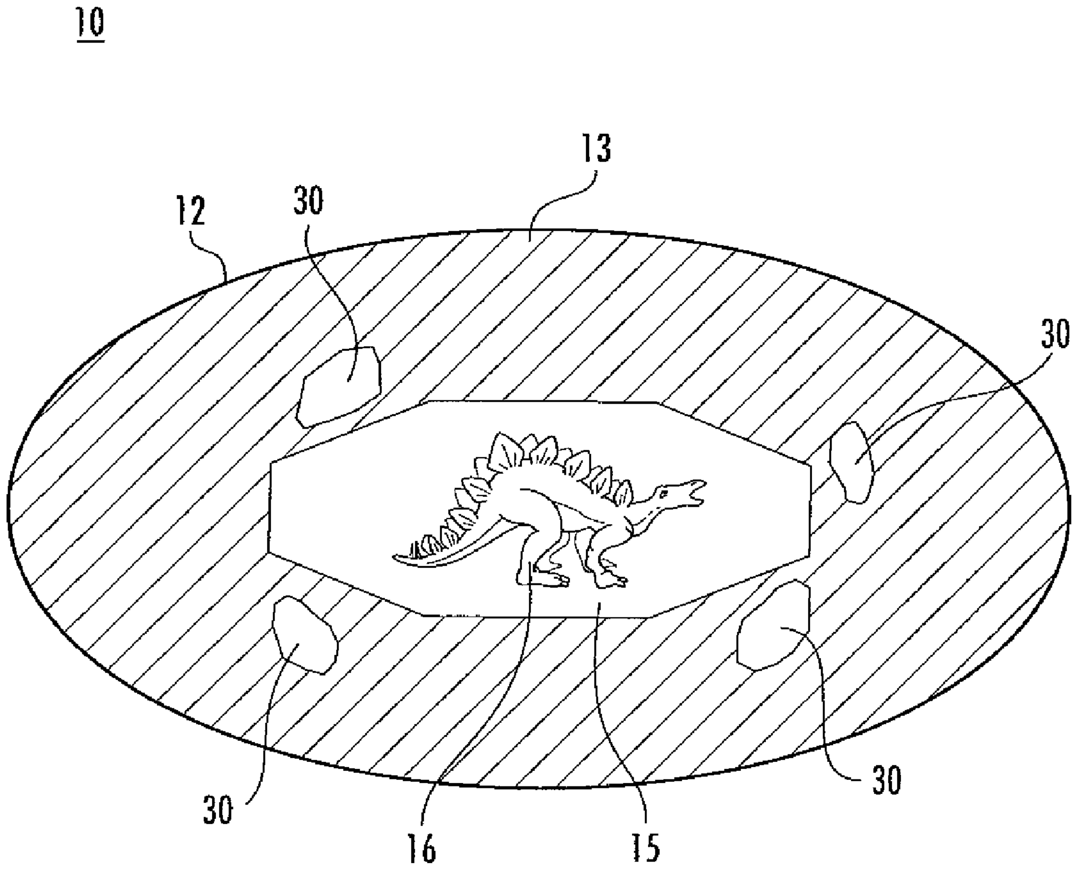
FIG. 3 is a schematic diagram of an alternate embodiment of the color changing bar soap.

FIG. 3 is an alternate embodiment in which inner layer 14 is replaced with one or more color changing tablets 30. Color changing tablets 30 are positioned within outer layer 13 adjacent or near toy capsule 15 or toy 16. Color changing tablets 30 can be formed of sodium bicarbonate having various color tinting. An example composition of the color changing material is sodium carbonate, sodium bicarbonate, citric acid, lactose, polyethylene glycol, and mineral oil.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. Color changing bar soap comprising:

a body formed of an outer layer;

a toy or toy capsule containing a toy encased by said outer layer; and one or more tablets being encased by said outer layer and being formed of a color changing material, said tablets being positioned adjacent or near said toy or toy capsule, said color changing material comprising sodium bicarbonate wherein upon exposure to moisture of said one or more tablets said color changing material is adapted to change the color of the remaining outer layer and/or water receiving said soap.

2. The soap of claim 1 wherein said outer layer is opaque.

3. The soap of claim 1 wherein the color tint is selected from FD&C Blue 1, FD&C Yellow 5, and D&C Red 33.

4. The soap of claim 1 wherein the color of said color changing material is related to said toy.

5. The soap of claim 1 wherein said toy is a meat eating dinosaur and the color of said color changing material is red.

6. The soap of claim 1 wherein said toy is a plant eating dinosaur and the color of said color changing material is green.

7. The soap of claim 1 wherein said toy is a flying dinosaur and the color of said color changing material is blue.

8. The soap of claim 1 wherein said toy is a dinosaur and said body has an egg shape.

9. The soap of claim 1 wherein said toy is an animal.

10. The soap of claim 1 wherein said toy is a vehicle.

11. The soap of claim 1 further comprising a housing for housing the color changing bar soap.

12. The soap of claim 11 wherein said toy is a dinosaur and said body has an egg shape and said housing is in the form of a crate or box.

13. The soap of claim 11 further comprising:

a material positioned within said housing beneath said soap for cushioning said soap.

14. The soap of claim 11 further comprising a document including indicia related to said toy.

15. The soap of claim 14 wherein said indicia is educational information.

16. The soap of claim 1 wherein said color changing material is formed of sodium carbonate and a further comprising color tint.

17. The soap of claim 1 wherein said color changing material further comprises citric acid.

* * * * *